United States Patent [19]

Volante et al.

[11] Patent Number: 4,582,914
[45] Date of Patent: Apr. 15, 1986

[54] PROCESS FOR THE PREPARATION OF HMG-COA REDUCTASE INHIBITORS

[75] Inventors: Ralph P. Volante, East Windsor; Thomas R. Verhoeven, Cranford; Meyer Sletzinger, North Plainfield; James M. McNamara, Rahway; Thomas M. H. Liu, Westfield; Edward G. Corley, Old Bridge, all of N.J.

[73] Assignee: Merck & Co., Inc., Rahway, N.J.

[21] Appl. No.: 696,965

[22] Filed: Jan. 31, 1985

[51] Int. Cl.$^4$ .................. C07D 309/30; C07C 69/738; C07C 69/732; C07C 69/716; C07C 69/675
[52] U.S. Cl. ..................................... 549/292; 560/53; 560/56; 560/59; 560/55

[58] Field of Search .................... 549/292; 560/53, 55, 560/56, 59

Primary Examiner—Norma S. Milestone
Attorney, Agent, or Firm—Joseph F. DiPrima; William H. Nicholson

[57] ABSTRACT

This invention relates to a novel process for the preparation of 3-hydroxy-3-methylglutarylcoenzyme A (HMG-CoA) reductase inhibitors which contain a 4-hydroxy-3,4,5,6-tetrahydro-2H-pyran-2-one moiety, such as compactin and mevinolin, by utilizing an alkyl 4-halo-3(S)-hydroxybutanoate as a chiral synthon for the stereospecific introduction of the 4-hydroxy-3,4,5,6-tetrahydro-2H-pyran-2-one moiety.

10 Claims, No Drawings

PROCESS FOR THE PREPARATION OF HMG-COA REDUCTASE INHIBITORS

BACKGROUND OF THE INVENTION

Endo et al., *J. Antibiotics*, XXIX, 1346 (1976) described a fermentation product, ML-236B, with potent antihypercholesterolemic activity which acts by inhibiting HMG-CoA reductase. This material, named compactin by Brown et al., *J. Chem. Soc., Perkin I*, 1165 (1976) was shown to have a desmethyl mevalonolactone partial structure and the stereochemistry was studied.

Shortly thereafter a chemically similar, natural product MK-803 (mevinolin), obtained by fermentation, was isolated and characterized, by Monaghan et al., U.S. Pat. No. 4,231,938. It has been shown to have the same desmethyl mevalonolactone partial structure and the absolute stereochemical configuration has been determined and described in EPO publication No. 0,022,478 of Merck & Co., Inc.

Totally synthetic analogs of these natural inhibitors have been prepared and described in Sankyo's U.S. Pat. No. 4,198,425 and Sankyo's U.S. Pat. No. 4,255,444 with no attempt being made to separate the stereo- and optical isomers. Subsequently, as described in Merck's EPO publication No. 0,024,348 and by Meyer, *Ann. Chem.*, (1979), pages 484–491, similar totally synthetic analogs were separated into their stereoisomers and optical enantiomers. Furthermore, it was shown in EPO publication No. 0,024,348 that essentially all of the HMG-CoA reductase activity resides in the 4(R)-trans species as is the case with the naturally occurring compounds compactin and mevinolin.

In most of the prior art processes for preparing the totally synthetic compounds, the lactone moiety of each compound had to be elaborated by a lengthy series of synthetic operations followed by very tedious and expensive chromatographic separation of the cis, trans racemates, or enantiomers, following which, the inactive cis-isomer would be discarded.

A process for the preparation of the lactone ring system in the correct optically active form was recently reported by Majewski et al., *Tetrahedron Lett.*, 1984, 2101–2104 utilizing a (3S,5S) iodoketal of the following formula:

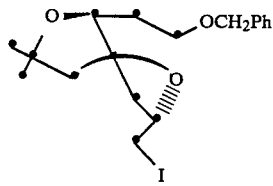

Additionally, a process for the preparation of HMG-CoA reductase inhibitors using alkyl 5(R),6-epoxy-3(R)-(alkoxy)hexanoate as a chiral synthon for the stereospecific introduction of 4-hydroxy-3,4,5,6-tetrahydro-2H-pyran-2-one moiety is disclosed and claimed in U.S. patent application Ser. No. 673,231, filed Nov. 19, 1984.

Further, filed contemporaneously herewith is U.S. patent application Ser. No. 696,963 wherein a process for the preparation of HMG-CoA reductase inhibitors using alkyl 4-cyano-3(R)-hydroxybutanoate as a chiral synthon for the 4-hydroxy-3,4,5,6-tetrahydro-2H-pyran-2-one moiety is described and claimed.

DETAILED DESCRIPTION OF THE INVENTION

This invention relates to a novel process for the preparation of antihypercholesterolemic agents of the following general structural formula (I):

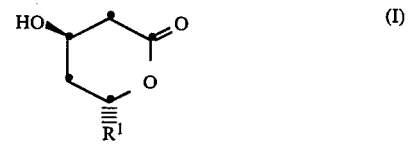

wherein $R^1$ is selected from the group consisting of:
(a)

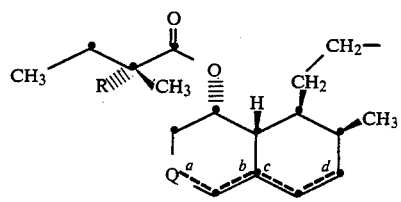

wherein Q is

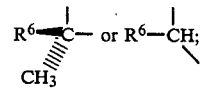

$R^6$ is H or OH;

R is hydrogen or methyl, and a, b, c, and d represent optional double bonds, except when a and c are double bonds, $R^6$ is not OH, especially wherein b and d represent double bonds or a, b, c, and d are all single bonds; or (b)

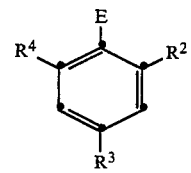

wherein E is —$CH_2$—, —$CH_2CH_2$— or —CH=CH—; $R^2$ and $R^3$ are independently $C_{1-3}$ alkyl or halo (F, Cl or Br) and $R^4$ is hydrogen, phenyl, benzyloxy, substituted phenyl or substituted benzyloxy in which the phenyl group in each case is substituted with one or more substituents selected from $C_{1-3}$ alkyl and halo, which comprises:

(A) reacting a compound of the formula (II):

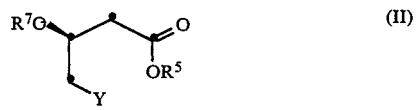

wherein Y is chloro, bromo or iodo; $R^5$ is $C_{1-5}$ alkyl or benzyl and $R^7$ is $C_{1-5}$ alkyl, benzyl, $C_{2-5}$ alkoxyalkyl, such as $CH_3OCH_2$, $C_{3-6}$ alkoxyalkoxyalkyl, such as $CH_3OCH_2CH_2OCH_2$, tri-$C_1$-$C_5$-alkylsilyl, such as tert-butyldimethylsilyl or trimethylsilyl, or tetrahydropyranyl with a compound of the formula (III):

wherein $R^1$ is defined above and $R^8$ is $C_{1-5}$ alkyl, benzyl, $C_{2-5}$ alkoxyalkyl, $C_{3-6}$ alkoxyalkoxyalkyl, tri-$C_{1-5}$-alkylsilyl or tetrahydropyranyl, in the presence of a non-nucleophilic base to afford a compound of the formula (IV):

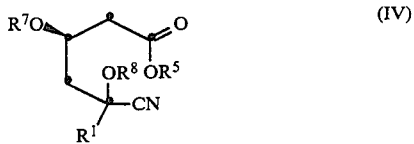

(B) removing the $R^7$ and $R^8$ group by suitable methods known in the art [T. Greene, *Protective Groups in Organic Synthesis*, John Wiley & Sons, 1981, pp. 10-86] or with an organoboronhalide with a concomitant conversion of the geminal cyanohydrin to a ketone to afford a compound of the formula (V):

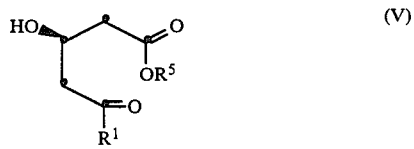

(C) stereospecifically reducing the ketone function in a compound of formula (V) under standard conditions to afford a compound of the formula (VI):

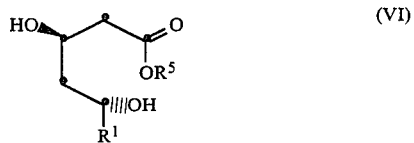

and (D) lactonizing the compound of the formula (VI) either under standard acid conditions or by first saponifying the ester followed by acidic treatment to afford the compound of the formula (I).

In a preferred embodiment, the compounds prepared by the process of this invention are those compounds of the formula (I) wherein $R^1$ is (a) and $R^6$ is hydrogen and R is hydrogen or methyl and b and d represent double bonds or a, b, c and d are single bonds.

In a second preferred embodiment, the compounds prepared by the process of this invention are those compounds of the formula (I) wherein $R^1$ is (b), $R^2$ and $R^3$ independently are chloro, fluoro or methyl and $R^4$ is 4-fluoro-3-methylphenyl or 4-fluorobenzyloxy. The most preferred compounds are those wherein (1) E is —CH═CH—, $R^2$ and $R^3$ are methyl and $R^4$ is 4-fluoro-3-methylphenyl; and (2) E is —CH═CH—, $R^2$ and $R^3$ are methyl and $R^4$ is 4-fluorobenzyloxy.

The reaction of the compound of the formula (II) with the compound of the formula (III) is conducted at a temperature between $-78°$ and $0°$ C., preferably at $-78°$ C. with warming to $-20°$ C. for a period of from 1 to 12 hours, most preferably 1 hour at $-78°$ C. and 1 hour at $-23°$ C., in the presence of a non-nucleophilic base and an inert solvent. Exemplifying such non-nucleophilic bases are alkyl metals, such as butyllithium and alkali metal amides wherein the alkali metal is selected from Li, Na or K and amide is selected from di-$C_{1-5}$-alkylamide, and pyrrolidide. Illustrative of such inert solvents are: ethers or thioethers or mixtures thereof, such as diethyl ether, tetrahydrofuran, dimethoxyethane, dimethylsulfide and the like.

The amounts of reactant that are employed in this reaction may vary between 1.0 and 1.5 equivalents of the compound of the formula (II) to each equivalent of the compound of the formula (III) in the presence of 1.0 to 1.25 equivalents of base. However, 1.1 equivalents of the compound of the formula (II) and 1.1 equivalents of base are preferred. The compound of the formula (II) wherein Y is iodo, $R^5$ is $C_{1-5}$ alkyl and $R^7$ is tert-butyldimethylsilyl; the compound of the formula (III) wherein $R^8$ is tetrahydropyranyl; and the base is n-butyllithium are preferred.

The removal of the $R^7$ and $R^8$ protecting groups and the conversion of the geminal cyanohydrin to a ketone is conducted at elevated temperature between 55° and 70° C., preferably at 65° C., for a period of 48 and 60 hours, preferably 48 hours under aqueous acid conditions. The acids which may be utilized in this reaction include organic acids, such as acetic, propionic, trichloroacetic, toluenesulfonic and the like, and inorganic acids, such hydrochloric, sulfuric and the like. The reaction may also be conducted in the presence of water soluble organic solvents, such as tetrahydrofuran, glyme and the like. The preferred aqueous acidic conditions are achieved with acetic acid, water and tetrahydrofuran.

Alternatively, the removal of the $R^7$ and $R^8$ protecting groups may be conducted at a temperature between $-78°$ and $0°$ C., preferably at $-78°$ for a period from 1 to 12 hours, preferably 1 hour in an inert solvent in the presence of an organoboron halide. Illustrative of such inert solvents are: chlorinated hydrocarbons, such as, methylene chloride, chloroform, dichloroethane or low melting mixtures thereof and the like.

The organoboron halide reactant is represented by the following formula:

$$R^9R^{10}BX$$

wherein $R^9$ and $R^{10}$ independently are $C_{1-4}$ alkyl, phenyl or when taken together with the boron atom to which they are attached form a 5, 6 or 7 membered ring or a bicyclic ring and X is chloro or bromo. The preferred organoboron halide is dimethylboron bromide. The amount of the organoboron halide utilized may vary between 1 and 10 equivalents for each equivalent of the compound of the formula (IV), with 4 equivalents being preferred. The conversion of the geminal cyanohydrin is then conducted by the addition of dilute aqueous acid to the reaction mixture.

The stereospecific reduction of the compound of the formula (V) is conducted according to the procedures disclosed and claimed in U.S. patent application Ser. No. 616,530, filed June 4, 1984, now abandoned which employs trialkylborane and sodium borohydride at low temperatures, to afford compounds of the formula (VI).

The lactonization of the compound of the formula (VI) may be conducted by saponifying the ester moiety with an alkali hydroxide in aqueous alcohol and then acidifying the reaction mixture with aqueous acid and azeotropically removing the water from the reaction mixture.

Alternatively, the lactonization of the compound of the formula (VI) is conducted at a temperature between 0° and 25° C., preferably at ambient temperature, for a period of from 1 to 12 hours, preferably 3 hours in an inert solvent with a catalytic amount of an acid. Illustrative of such inert solvents are: hydrocarbons, such as, hexane, toluene, benzene, cyclohexane and the like; and ethers, such as, diethylether, tetrahydrofuran, dimethoxyethane and the like. Illustrative of such acids are organic acids, such as, p-toluenesulfonic, benzenesulfonic and the like and inorganic acids, such as, hydrochloric. The preferred acid utilized in the lactonization is p-toluenesulfonic acid.

The starting materials are either known or readily prepared according to the synthetic pathways described below.

The compounds of the formula (III) are readily prepared from an appropriately substituted aldehyde by treatment with aqueous sodium cyanide to form the cyanohydrin, which is then converted to the desired starting material by the protection of the hydroxy group. Alternatively, the appropriately substituted aldehyde may be reacted with trialkylsilylcyanide to form a desired starting material in one step.

The appropriately substituted aldehyde precursors to the compounds of the formula (III) wherein $R^1$ is (b) are known in the art (see U.S. Pat. Nos. 4,375,475 and 4,322,563). For the compounds of the formula (III) wherein $R^1$ is (a), Tetrahedron Lett., pp. 1373-6 (1983) and Tetrahedron Lett., pp. 1655-8 (1984) describe procedures for preparing compounds which can be readily converted into the appropriate substituted aldehyde precursors using standard chemical transformations.

The compounds of the formula (II), wherein Y, $R^5$ and $R^7$ are defined above, are readily prepared according to the following synthetic pathway from isoascorbic acid:

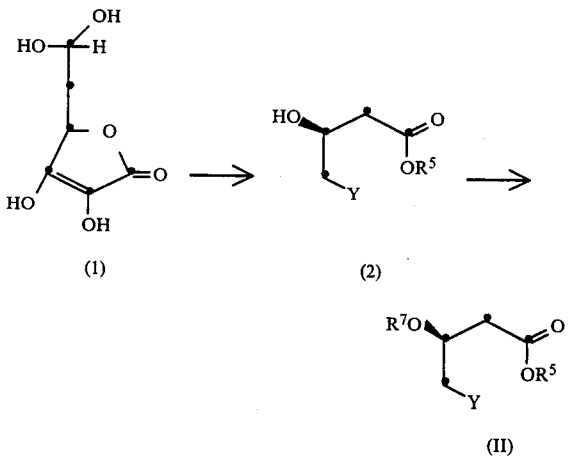

Isoascorbic acid (1) is degraded utilizing the methodology of Buck et al., Acta. Chem. Scand., B, 37, 341 (1983) to afford alkyl 4-halo-3(S)-hydroxy butanoate (2) which is then reacted with an appropriate reagent to protect the hydroxy function and yield the compounds of the formula (II).

The following Examples illustrate the present invention and as such are not to be considered as limiting the invention set forth in the claims appended hereto.

EXAMPLE 1

Preparation of 6-[2-(4'-fluoro-3,3',5-trimethyl-[1,1'-biphenyl]-2-yl)ethenyl]-3,4,5,6-tetrahydro-4-hydroxy-2H-pyran-2-one (a): E-4-(4'-fluoro-3,3',5-trimethyl-[1,1'-biphenyl]-2-yl)-2-tetrahydropyranyloxy-3-butenoic acid nitrile (1a)

E-3-(4'-Fluoro-3,3',5-trimethyl-[1,1'-biphenyl]-2-yl)-2-propenal (5.4 g, 20 mmol) was dissolved in acetonitrile (20 ml) and trimethylsilylcyanide (2.4 ml, 20 mmol) was added via a syringe at ambient temperature. The mixture was stirred at 22° C. and zinc bromide (5 mg) was added. After 30 minutes at 22° C., the mixture was diluted with 3N hydrochloric acid (25 ml) and after an additional 30 minutes was diluted with water (50 ml). The reaction mixture was extracted with methylene chloride (2×50 ml), the organic phases combined, dried over sodium sulfate and concentrated in vacuo. The residual oil was dissolved in methylene chloride (75 ml), dihydropyran (6.4 g, 40 mmol) was added and then p-toluenesulfonic acid (5 mg) was added. The reaction mixture was stirred for 30 minutes at 22° C. and neutralized with saturated aqueous sodium bicarbonate (50 ml). The organic phase separated, washed with saturated aqueous sodium chloride, dried over sodium sulfate and concentrated in vacuo. The resulting crude product was purified by chromatography (silica gel) eluted with methylene chloride:hexane (1:1) to afford the desired product 1(a) with satisfactory nmr and ir spectra.

(b): Methyl 7-[(4'-fluoro-3,3',5-trimethyl-1,1'-biphenyl)-2-yl]-5-cyano-5-tetrahydropyranyloxy-3-t-butyldimethylsilyloxy-6(E)-heptenoate 1(b)

To the compound 1(a) (379 mg, 1.0 mmol) was dissolved in tetrahydrofuran (1 ml) at −78° C. under nitrogen was added via syringe 1.6M n-butyllithium in hexane (0.7 ml). The reaction mixture was stirred at −78° C. for 30 minutes and 1,3-dimethyl-2-imidazolidinone (100 μl) was added. The reaction mixture was warmed to −35° C. and methyl 4-iodo-3(S)-t-butyldimethylsilyloxybutanoate (400 mg, 1.1 mmol), prepared according to Example 2, in tetrahydrofuran (10 ml) was added. The reaction mixture was stirred for 2 hours and then allowed to warm to 0° C. The reaction was quenched with water (10 ml) and then the reaction mixture was extracted with methylene chloride (2×20 ml). The extracts were combined, dried over sodium sulfate and concentrated in vacuo to afford the crude product which was purified by chromatography (silica gel eluted with methylene chloride) to afford the desired product as mixture of diastereomers 1(b) with satisfactory nmr and ir spectra.

(c): Methyl 7-[(4'-fluoro-3,3',5-trimethyl-1,1'-biphenyl)-2-yl]-3(R)-hydroxy-5-oxo-6(E)-heptenoate 1(c)

The diastereomers 1(b) (300 mg, 0.5 mmol) were dissolved in a mixture of acetic acid, tetrahydrofuran, and water (10 ml, 4:1:1) and heated at 60° for 24 hours. The reaction mixture was diluted with water (50 ml) and then extracted with methylene chloride (3×25 ml). The extracts were combined, washed with water (25 ml), dried over sodium sulfate, and concentrated in vacuo to yield the desired compound 1(c) as a single diastereomer with satisfactory nmr and ir spectrum.

(d): Methyl 7-][(4'-fluoro-3,3'-5-trimethyl-1,1'-biphenyl)-2-yl]-3(R),5(S)-dihydroxy-6(E)-heptenoate 1(d)

After 5 minutes at ambient temperature, a solution of the compound 1(c) (3.0 g, 7.8 mmol) and triethylborane (0.92 g, 9.4 mmol) in tetrahydrofuran (22 ml) under nitrogen was cooled to −78° C. To the solution was added sodium borohydride (350 mg, 9.25 mmol), followed by the addition over 15 minutes of methanol (5 ml) while maintaining the temperature below −65° C. The reaction was carefully quenched at 20° C. with a solution of 30 percent hydrogen peroxide (15 ml) and water (30 ml). The reaction mixture was extracted with ethyl acetate (50 ml). The organic phase was washed with 1N aqueous hydrochloric acid (25 ml), water (25 ml) and pH 7 buffer solution (25 ml), then dried over sodium sulfate and concentrated in vacuo. The oily residue was crystallized in hexane and triturated in hexane to afford the compound 1(d) as a white solid (m.p. 78°–80° C.). High pressure liquid chromatography assay indicates a purity of 99% of the desired product.

(e): 6-[2-(4'-fluoro-3,3',5-trimethyl-[1,1'-biphenyl]-2-yl)-ethenyl]-3,4,5,6-tetrahydro-4(R)-hydroxy-2H-pyran-2-one To a suspension of the compound 1(d) (10.97 g) in water (60 ml) was added 0.5N sodium hydroxide (142 ml) and the suspension stirred at ambient temperature until a solution was obtained. The solution was diluted with methylene chloride (250 ml) and then acidified with 3N hydrochloric acid (25 ml). The phases were separated and the aqueous phase extracted with methylene chloride (130 ml). The combined organic phase was washed with water (250 ml) and saturated aqueous sodium chloride (250 ml). The aqueous phases were backwashed with methylene chloride (80 ml) and the combined organic phases were dried over sodium sulfate and then concentrated in vacuo at less than 30° C. The residue was dissolved in toluene and heated at 90° C. for 9 hours under nitrogen. The toluene was removed in vacuo and the residue dissolved in diethyl ether (10 ml). To the solution was added hexane (15 ml) and the solution cooled to 0°–5° C. to afford the desired compound as a precipitate. The precipitate was washed with hexane:diethyl ether (3:2) to yield the desired product as a white solid.

EXAMPLE 2

Preparation of Methyl-4(R)-iodo-3(S)-t-butyldimethylsilyloxybutanoate (a): Methyl 4-bromo-3(S)-hydroxybutanoate 2(a)

A solution of D-(−)-isoascorbic acid (35.22 g, 0.20 mole) in water (500 ml) was treated with calcium carbonate (40 g, 0.40 mole). The mixture was then stirred at 10° C. and 30 percent hydrogen peroxide (80 ml) was slowly added. The reaction mixture was then allowed to warm slowly to 20° C. at which point the reaction became exothermic. The reaction mixture was then stirred at 45°–50° C. for 40 minutes and then treated with activated carbon (8 g). The reaction was then heated at 95°–100° C. to destroy the excess peroxide. When the solution gave a negative starch-iodide test (about 45 minutes) it was filtered through diatomaceous earth. Treatment of the filtrate with potassium carbonate (13.83 g, 0.10 mol) precipitated the calcium as the carbonate. The calcium carbonate was filtered and the filtrate concentrated in vacuo to about 45 ml. The concentrate was then treated to the slow addition of methanol (400 ml). The potassium-D-erythronate that precipitated was collected by filtration.

Compound 2(a) was prepared from potassium-D-erythronate in the manner described by Bock et al., *Acta. Chem. Scand.*, 341 (1983).

(b): Methyl 4-bromo-3(S)-t-butyldimethylsilyloxybutanoate 2(b)

The compound 2(a) (16.3 g, 82.7 mmol) was dissolved in dimethylformamide (83 ml) and treated with t-butyldimethylchlorosilane (13.71 g, 91 mmol), imidazole (12.39 g, 182 mmol) and 4-dimethylaminopyridine (25 mg, 0.2 mmol). The solution was stirred at 20°–25° C. for 12 hours, and then 3N hydrochloric acid (30 ml) was added. The reaction mixture was then partitioned between hexane/H$_2$O (400 ml each). The aqueous layer was washed with 200 ml hexane. The combined hexane layers were washed with water (400 ml), then with saturated brine (400 ml) and then dried over sodium sulfate. Concentration in vacuo gave the compound 2(b) as a colorless oil.

(c): Methyl 4-iodo-3(S)-t-butyldimethylsilyloxybutanoate 2(c)

The compound 2(b) (622 mg, 2.0 mmol) was dissolved in methylethylketone (25 ml) and sodium iodide (1.5 g, 10.0 mmol) was added. The reaction mixture was heated to reflux for 16 hours and then the solvent removed in vacuo. The residue was partitioned between water (50 ml) and methylene chloride (50 ml) and the organic phase was washed with 5 percent aqueous sodium sulfite solution (25 ml). The organic phase was dried over sodium sulfate and concentrated in vacuo to give compound 2(c) as a clear oil with satisfactory nmr and ir spectra.

EXAMPLES 3–12

Utilizing the general procedures of Example 1 and starting from the appropriately substituted compounds of the formula (III) and 4(R)-iodo-3(S)-t-butyldimethylsilyloxybutanoate the following compounds of the formula (I) are prepared:

| Compound Number | R$^1$ |
| --- | --- |
| 3 | (structure) |
| 4 | (structure) |

What is claimed is:

1. A process for the preparation of compounds of the following structural formula (I):

$$HO\underset{\underset{R^1}{\equiv}}{\overset{\displaystyle{\diagdown}}{\phantom{X}}}\phantom{XX}\overset{O}{\diagdown}\phantom{X}O \qquad (I)$$

wherein $R^1$ is selected from the group consisting of:

(a)

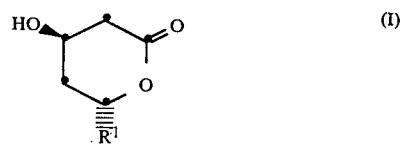

wherein
Q is

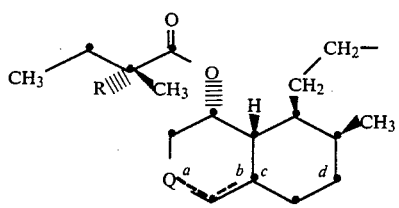

$R^6$ is H or OH;
R is hydrogen or methyl, and a and c except when $R^6$ is OH, or b and d represent double bonds or all of a, b, c and d are single bonds; or (b)

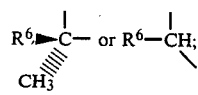

wherein E is —CH$_2$—, —CH$_2$CH$_2$— or —CH=CH—; $R^2$ and $R^3$ independently are C$_{1-3}$ alkyl fluoro, chloro or bromo; and $R^4$ is phenyl, benzyloxy, substituted phenyl or substituted benzyloxy in which the phenyl group in each case is substituted with one or more substituents selected from C$_{1-3}$ alkyl, fluoro, bromo or chloro;
which comprises:
(A) reacting a compound of the formula (II):

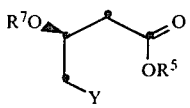 (II)

wherein Y is chloro, bromo or iodo; $R^5$ is $C_{1-5}$ alkyl or benzyl; and $R^7$ is $C_{1-5}$ alkyl, benzyl, $C_{2-5}$ alkoxyalkyl, $C_{3-6}$ alkoxyalkoxyalkyl, tri-$C_1$-$C_5$-alkylsilyl or tetrahydropyranyl
with a compound of the formula (III):

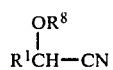 (III)

wherein $R^1$ is defined above; and $R^8$ is $C_{1-5}$ alkyl, benzyl, $C_{2-5}$ alkoxyalkyl, $C_{3-6}$ alkoxyalkoxyalkyl, tri-$C_{1-5}$-alkylsilyl or tetrahydropyranyl; in the presence of a non-nucleophilic base to afford a compound of the formula (IV):

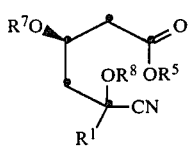 (IV)

(B) removing the $R^7$ and $R^8$ group under aqueous acidic conditions or with an organoboron halide with a concomitant conversion of the geminal cyanohydrin to a ketone to afford a compound of the formula (V):

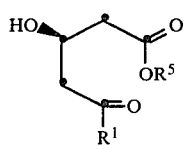 (V)

(C) stereospecifically reducing the ketone function in a compound of the formula (V) with tri-$C_{1-5}$-alkylborane and alkali metal borohydride at low temperatures to afford a compound of the formula (VI):

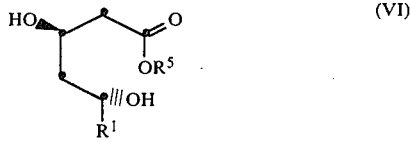 (VI)

(D) lactonizing the compound of the formula (VI) either under acidic conditions or by first saponifying the ester followed by acidic treatment to afford the compound of the formula (I).

2. A process of claim 1 wherein $R^1$ is (a).

3. A process of claim 2 wherein $R^6$ is hydrogen and R is hydrogen or methyl and b and d represent double bonds or each of a, b, c and d is a single bond.

4. A process of claim 1 wherein $R^1$ is (b).

5. A process of claim 4 wherein $R^2$ and $R^3$ independently are chloro, fluoro or methyl and $R^4$ is 4-fluoro-3-methylphenyl or 4-fluorobenzyloxy.

6. A process of claim 5 wherein E is —CH=CH—, $R^2$ and $R^3$ are methyl.

7. A process of claim 5 wherein E is —CH=CH—; $R^2$ and $R^3$ are methyl and $R^4$ is 4-fluoro-3-methylphenyl.

8. A process of claim 1 wherein the non-nucleophilic base of Step (A) is an alkali metal or an akali metal amide; the aqueous acid conditions of Step (B) are achieved with an organic acid, water and a water soluble solvent; the lactonization of Step (D) utilizes an alkali hydroxide in alcohol to saponify the ester.

9. A process for the preparation of a compound of the formula (V) which comprises the Steps (A) and (B) of claim 1.

10. A process for the preparation of a compound of the formula (VI) which comprises the Steps (A), (B) and (C) of claim 1.

* * * * *